US006342520B1

(12) United States Patent
Zamoyski

(10) Patent No.: US 6,342,520 B1
(45) Date of Patent: Jan. 29, 2002

(54) LOCALLY INJECTABLE CHEMOTHERAPEUTICS

(76) Inventor: Mark Zamoyski, 988 Foothill Dr., San Jose, CA (US) 95123

( * ) Notice: Subject to any disclaimer, the term of this patent is extended or adjusted under 35 U.S.C. 154(b) by 0 days.

(21) Appl. No.: 09/699,913

(22) Filed: Oct. 30, 2000

(51) Int. Cl.$^7$ .............................................. A61K 31/335
(52) U.S. Cl. ...................... 514/450; 514/450; 514/452; 514/453; 514/456; 514/460; 514/475; 604/187
(58) Field of Search .................................. 514/450, 452, 514/453, 456, 460, 475; 604/187

(56) References Cited

U.S. PATENT DOCUMENTS

| | | |
|---|---|---|
| 4,744,981 A | 5/1988 | Pavanasasivam |
| 4,906,452 A | 3/1990 | Sivam |

OTHER PUBLICATIONS

Fauci et al, Harrison's, Principles of internal medicine, 14$^{th}$ Edition, McGraw Hill (1998) pp. 521, 527–534, 554, 566–567.

Alberts et al., Molecular Biology of The Cell, Third Edition, Garland Publishing (1994) pp. 520, 803–806, 866–867, 869–870, 874–876, 894–897, 958–959, 1271–1272, 1278–1279.

Okazaki et al., "Antiviral Activity of Macrocyclic Trichothecene Mycotoxins" Agricultural and Biological Chemistry, vol. 53 pp. 1441–1443 (1989).

Okazaki et al, "Inhibition By Trichothecene Mycotoxins of Replication of Herpes Virus Type 2", Agricultural and Biological Chemistry vol. 52 pp. 795–801 (1988).

Tani et al., Antiviral Activity of Trichothecene Mycotoxins Against Herpes Simplex Type 1 and 2, Microbiol. Immunol., 39(8) pp. 635–637 (1995).

Amriid, "Understanding The Threat" Printout From Us Amriid Website, 7 pages (1999).

Niehs Press Release, "Niehs, CDC Fund Study of Fungus Fatal to Cleveland Infants"1 page, (1998).

University of Minnesota, Department of Environmental Health and Safety, "Stachybotres", Printout from Website, 1 page (1999).

UCLA, "What is PET", Printout from Website, 12 pages (2000).

Magainin Pharmaceuticals Inc., "Squalamine:Synergy Hypothesis" Printout from informed investors conference, 1 Page (2000).

NCI, "Cancer Trials–Angiogenesis Inhibitors in Cancer Research" Printout from Website, 1 page (1999).

*Primary Examiner*—Frederick Krass

(57) ABSTRACT

Sesquiterpenoid compounds and method for using such compounds to inhibit proliferation of malignant cells without inducing appreciable systemic cytotoxicity are disclosed. The compositions and methods presented also greatly reduce the duration of administration regimens compared to prior art and provide novel synergistic uses in combination with prior art chemotherapeutics.

7 Claims, No Drawings

LOCALLY INJECTABLE CHEMOTHERAPEUTICS

BACKGROUND—SUMMARY

Certain Sesquiterpenoid compounds (macrocyclic trichothecenes) and methods for using such compounds to inhibit proliferation of malignant cells without inducing appreciable systemic cytotoxicity are disclosed. The compositions and methods presented also greatly reduce the duration of administration regimens compared to prior art and provide novel synergistic uses in combination with prior art chemotherapeutics.

BACKGROUND

Prior Art Chemotherapeutics (HPIM pits. 527–534)

Most chemotherapeutic agents in use today are cell cycle active; that is, they are cytotoxic mainly to actively cycling cells. Alkylating agents are among the most widely used anti tumor agents and are efficient at cross-linking DNA, leading to strand breakage. Alkylating agents include cyclophosphamide, ifosfamide, melphalan, busulfan, mechlorethamine (nitrogen mustard), chlorambucil, thiotepa, carmustine, lomustine as well as platinum compounds such as cisplatin and carboplatin, which are not true alkylating agents also lead to covalent cross linking of DNA. Purine/pyrimidine analogs/antimetabolites induce cytotoxicity by serving as false substrates in biochemical pathways. They include cytarabine, fluorouracil, gemcitabine, cladribine, fludarabine, pentostatin, hydroxyurea, and methotrexate. Topoisomerase inhibitors interfere with the enzymes topoisomerase 1 and topoisomerase 2, responsible for mediating conformational and topological changes in the DNA required during transcription and replication. These agents include daunorubicin, doxorubicin, idarubicin, etoposide, teniposide, dactinomycin, and mitoxantrone. Plant Alkaloids include vincristine, vinblastine, and vinorelbine which inhibit microtubule assembly by binding to tubulin and docetaxel and paclitaxel which function by stabilizing microtubules and preventing their disassembly. Antitumor Antibiotics include bleomycin that induces DNA strand breakage through free radical generation and Mitomycin C which cross links DNA. Other Agents include dacarbazine and procarbazine which act as alkylating agents to damage DNA and L-Asparaginase, the only enzyme used as a anti tumor agent, which acts by depletion of extracellular pools of asparagine.

Prior art chemotherapeutics typically work by one highly specific pathway to damage or prevent DNA replication. Compositions of present invention work by several pathways that have direct, indirect, and synergistic effects against cancer (discussed later in the application).

Principles of Chemotherapeutic Administration (HPIM pgs. 527–528)

Chemotherapeutic agents exhibit a dose response effect. At sufficiently low concentrations no cytotoxicity is observed. At increasing concentrations, cell kill is proportional to drug exposure. At high concentrations, the effect reaches a plateau. Drugs that are cell cycle active, but not phase specific, characteristically have steep dose response curves: An increase in the drug concentration by an order of magnitude or more results in a proportional increase in tumor cell kill. By contrast, the dose response curve of phase specific agents typically is linear over only a narrow range. These agents are less suitable for dose escalation and increased tumor cell kill is observed after prolonged exposure as a larger percentage of the tumor cells enter the cell cycle.

Chemotherapy employs two principles in administration: Therapeutic Index Dosaging and Cyclical Administration. The therapeutic index represents the difference between the response of the tumor and response of normal tissue for a given dose of chemotherapeutic. Normal cells are also susceptible to the cytotoxic effects of chemotherapeutic drugs and exhibit a dose-response effect, but the response curve is shifted relative to that of malignant cells (HPIM p. 528, FIG. 86-3). This difference represents the therapeutic index. The toxicity to normal tissue that limits further dose escalation is the "dose-limiting toxicity". The dose just below this point is the "maximum tolerated dose". Proliferative normal tissues such as the bone marrow and gastrointestinal mucosa are generally the most susceptible to chemotherapy-induced toxicity.

Cyclical administration is used to allow normal rapidly proliferating tissue such as hemopoietic stem cells to recover and blood counts to reach their normal levels. Most chemotherapeutics are administered in cycles of 21 to 28 days and 6 to 8 cycles are typically used. The number of administration cycles required to completely eradicate a tumor is dependent on the tumor kill rate of the therapeutic. To completely eradicate a tumor it is necessary to get below the mathematical 1 surviving cell number ("log cell kill model" developed by Skipper and coworkers, described in HPIM p. 527, and incorporated herein by reference). As an example, to kill a 10 billion cell tumor with a chemotherapeutic that kills 95% of the tumor cells each administration cycle (5% survive) would require 8 cycles of chemotherapy (i.e. $10,000,000,000 \times 0.05 \times 0.05 \times 0.05 \times 0.05 \times 0.05 \times 0.05 \times 0.05 \times 0.05 = 0.39$). However, this assumes the tumor does not grow in the period when the chemotherapeutic is not administered ("off" period).

Administration methods for therapeutics of present invention, for cytotoxic activity against target cancer cell populations, vary radically from prior art in that therapeutics of present invention are not administered into general circulation but administered interstitially at the tumor site. Although compositions of current invention are cell cycle active, because they are administered interstitially and rapidly internalize into cells, they do not induce the systemic cytotoxicity of prior art chemotherapeutics.

Current Invention as Measured by Prior Art Standards Against Prior Art Chemotherapeutics Under prior art standards, the larger the therapeutic index between cytotoxicity to tumors versus normal tissue the "better" a chemotherapeutic was, as it has greater specificity to the cancer cells (HPIM p. 528 FIG. 86-3). The "normal tissue response" line for computation of therapeutic index as defined by prior art however, is the most susceptible or rapidly proliferating normal tissue in the body that the chemotherapeutic reached—and that would normally be cells in the bone marrow. There are roughly 210 different types of epithelial cells in the body and when using systemic administration methods as in prior art, there are theoretically ~210 "normal tissue response" curves that exist, with only the leftmost one (e.g. bone marrow) considered for therapeutic index computation.

Because therapeutics of current invention are administered substantially interstitially and localized, the "normal tissue response" curve for computing therapeutic index is based on the surrounding tissue into which it is injected (e.g into breast, lung, brain, etc . . . ) which is not normally a rapidly proliferating tissue and by definition would be situated well to the right of the comparable bone marrow or gastrointestinal mucosa lines. Present invention thus limits the theoretical number of potential response lines to a very small subset of the ~210 possible cell types, eliminating the known "far left" normal response curves of cell types such as bone marrow or gastrointestinal mucosa. Thus, the therapeutic index would be much larger for compositions of present invention simply because the "normal tissue response" line would be shifted over to the right, increasing the therapeutic index gap, making compositions of present invention "better" under prior art standards.

Trichothecenes

Fungi of the genera Fusarium, Myrotecium, Trichoderma, Stachybotrys and others produce Trichothecene mycotoxins. Trichothecenes constitute a family of fungal sesquiterpene epoxides that inhibit protein synthesis. Trichothecene mycotoxins are low molecular weight (250–700 daltons), non volatile compounds, and of over 150 trichothecenes have been identified. There are two broad classes: those that have only a central Sesquiterpenoid structure and those that have an additional macrocyclic ring (simple and macrocyclic trichothecenes, respectively). As used in this application, "biologically active agent", "mycotoxins", "trichothecene", or "therapeutics" are defined as either simple or macrocyclic trichothecenes. A listing of molecular structures of representative simple and macrocyclic trichothecenes is included in U.S. Pat. Nos. 4,744,981 and 4,906,452, incorporated herein by reference. Trichothecenes are fast acting potent inhibitors of protein synthesis in eucaryotic cells. Their main effects are on rapidly proliferating tissues. The sesquiterpenoid ring binds to ribosomes, inhibiting protein synthesis. In macrocyclic trichothecenes, the macrocyclic ring enhances cell binding and internalization.

Since trichothecenes neither contain nor produce amino acids they escape detection by the human immune system. Since trichothecene molecules contain only carbon, hydrogen, and oxygen they are not be subject to proteolytic degradation as they do not contain amino acids and the associated nitrogen atoms to form a peptide bond. U.S. Pat. No. 4,906,452 (column 11 first paragraph) further discloses that some studies of the rates at which certain trichothecenes are converted into biologically inactive molecules (apotrichothecenes) found that macrocyclic trichothecenes are inactivated quite slowly and only by intracellular acid catalysis as might occur in lyzosomes.

Novelty of Present Invention Versus Prior Art Attempts to Use Trichothecene

The utility of trichothecenes against cancer has been established in prior art as well as the abject failure of administering Anguidine, a simple trichothecenes, by general circulation. In Phase II clinical trials of Anguidine the overall tumor response rate was low and there was considerable hematologic toxicity. U.S. Pat. Nos. 4,744,981 and 4,906,452 represent the prior art solution to this failure by attempting to enhance delivery of trichothecene to the tumor by using conjugates of trichothecene molecules and monoclonal antibodies as well as improving solubility through glycosylation. The present invention takes the novel, unobvious, and exactly opposite approach to resolve the systemic cytotoxicity issue. Current invention reverses the direction of administration over prior art, going from tissue to blood versus from blood to tissue. Current invention also embraces the use of non specific cellular internalization (exactly opposite from prior art), using this attribute to rapidly localize trichothecenes to the intra-organ, intercellular gap junction transport system to prevent distant lymphatic or circulatory transport and systemic cytotoxicity. Using principles of therapeutic index dosaging, the current invention uses normal surrounding tissue to "filter out" and retain the trichothecene, preventing it from entering general circulation. Current invention's reversing direction makes the things that work against you when administering into general circulation work for you in the reverse direction. One does not have a problem getting therapeutic to the tumor. The relative aqueous insolubility and cellular internalization properties work to localize the therapeutic in the tumor area (discussed in more detail later) and keep the therapeutic out of general circulation. Furthermore, present invention identifies specific members of the trichothecene family (and methods for finding others) that have demonstrated rapid internalization and localization attributes, a criteria that is now important because of the novel administration method.

Utility of Present Invention—Novel, Multiple, Mechanisms of Action versus Prior Art Chemotherapeutics Of the more than 30 chemotherapeutics in use today (described in the beginning of the patent application) none of them employ broad spectrum protein synthesis inhibition as a mechanism of action. This novel mechanism of action consequently also makes compositions and methods of current invention ideal for use with other chemotherapeutics in "combination chemotherapy" (as defined in HPIM pgs. 531–532). Furthermore, synergistic properties from using compositions of present invention in conjunction with other chemotherapeutics can reasonably be expected because of the pathways involved (e.g. anti drug resistance properties, oncogene suppression properties) as well as its use in special situations (e.g. large tumors) described later in this application.

There are several major advantages to using compositions of present invention over prior art chemotherapeutics and they relate, in part, to the multiple molecular pathways inhibited by compositions of present invention, in contrast to prior art chemotherapeutics which are generally limited to inhibiting only one highly specific pathway involved in DNA replication. The advantages are described below.

1) Direct Action Against Cancer Cells—Cytotoxicity

In therapeutically effective dosages, trichothecenes are toxic to all rapidly proliferative cells, which include cancer cells. Non cycling cells have as little as 20% of the protein synthesis activity of actively cycling cells. Interference with protein synthesis has lethal consequences for actively cycling cells in various phases of the cell cycle. Several pathways are likely involved with the observed cytotoxicity to actively cycling cells.

It has been shown that temporary disruption of spindle microtubules preferentially kills many abnormally dividing cells (MBOC p. 804). Microtubules are highly labile structures and are highly sensitive to concentrations of the protein tubulin for their rapid elongation and contraction (MBOC pgs. 803–805). Interfering, even slightly, with the concentrations of free tubulin by a protein synthesis inhibitor, would prevent the critical concentration required for polymerization (rapid elongation) and formation of the mitotic spindle required for cell division. Reducing tubulin concentrations at an inappropriate time in the cell's division cycle would cause premature depolymerization (rapid shrinking) of the microtubules at an inappropriate time which would literally result in portions of the DNA being torn apart. Prior art chemotherapeutics that work by disruption of spindle microtubules to kill cancer include vinblastine, vincristine, paclitaxel and docetaxel. Vincristine and vinblastine inhibit microtubule assembly by binding to tubulin and thus are cytotoxic predominantly during the M phase of the cell cycle. Paclitaxel and docetaxel stabilize microtubules preventing their disassembly.

Several key proteins need to be switched on at a high rate of synthesis at various stages of the cell cycle. Histones, which are required for formation of new chromatin, are made at a high rate only in S phase and the same is true for some enzymes that manufacture deoxyribonucleotides and replicate DNA (MBOC pgs. 866–867). In G1, large amounts of protein synthesis is required to grow the cell to nearly twice its size. Compositions of present invention interfere with all of these processes.

Therapeutics of present invention also interfere with the cell cycle control system and related downstream processes. The cell cycle control system is based on two key families of proteins. The first is the cyclin-dependent protein kinases (Cdk) which induce downstream processes by phosphorylating selected proteins on serines and threonines. The second is a family of specialized activating proteins called cyclins that bind to Cdk molecules and control their ability to phosphorylate appropriate target proteins. Without cyclin, Cdk is inactive (MBOC p. 869). There are two main classes of cyclins. G1 cyclins bind to Cdk molecules during G1 and are required for entry into S phase. Mitotic cyclins accumulate gradually during G2 and bind to Cdk to for a complex known as M-phase promoting factor (MPF). Past a critical threshold, MPF synthesis becomes an autocatalytic explosion, and a flood of active MPF induces downstream events through its protein kinase activity, including condensing the chromosomes, breaking down the nuclear envelope, and reorganizing the cytoskeleton to form the mitotic spindle (MBOC p. 876). Blocking protein synthesis in early interphase has been shown to inhibit cyclin production which prevents both the activation of MPF and the next mitosis (MBOC p. 874).

The purpose of the above examples is to contrast the multiple, powerful mechanisms of action provided by compositions of present invention versus the single highly specific mechanisms of action of prior art chemotherapeutics as described earlier in the background section. Additionally, there are several more novel mechanisms of actions that merit disclosing to facilitate an understanding of the novelty over prior art chemotherapeutics as well as related novel cyclical administration methods and novel internalization profiling methods described in the reduction to practice section of this application.

2) Direct Action Against Cancer Cells—Inhibition of Oncogene Product

Cancer happens through mutations that either disable genes responsible for inhibiting growth (tumor-suppressor genes) or mutations of genes that cause over expression or inappropriate expression of proteins responsible for growth (oncogenes). Cancers develop gradually from a single aberrant cell, progressing from benign to malignant tumors by the accumulation of a half-dozen or so (typically 5–10) of such independent genetic accidents ("lesions"). Over 60 potential oncogenes have been discovered so far and oncogene products include examples of practically every type of molecule involved in cell signaling related to growth (MBOC pgs. 1278–1279). Inhibiting overproduction of oncogenes growth factor proteins driving cancer cell growth would have two very important, novel roles in fighting cancer.

First, it would have an immediate impact on preventing a new division cycle from being initiated. It would prevent tumor growth at the very source, particularly for cancers that were primarily driven by overexpression of growth factors. As an example, lung cancer cells acquire a fairly large number of genetic lesions (perhaps 10 or more). Trichothecenes, as a preferential inhibitor of hyperactive protein synthesis, would inhibit overexpression of growth factor proteins coded for by these oncogenes. This property of trichothecenes would apply equally well to both small and non-small cell lung cancers as the profile of oncogenes related protein product is heavily dominated by protein overexpression (HPIM p. 554) and as summarized below:

| Oncogene Abnormalities | SCLC | NSCLC |
|---|---|---|
| myc family overexpression | >50% | >50% |
| bcl-2 overexpression | >75% | >50% |
| Her-2/neu overexpression | <10% | ~30% |
| Telomerase overexpression | >90% | >90% |
| ras mutations | <1% | ~30% |

Second, depriving cells of growth factors halts cell proliferation by rapidly dismantling the cell-cycle control system rather than simply stopping it (MBOC p. 897). When proliferating cells are deprived of growth factors they stop growing but continue to pass through the cell cycle until they reach the G1 phase (MBOC p. 895). Cells enter a $G_0$ state at the G1 checkpoint (i.e. if a cell is in early G1 it will stop at the G1 checkpoint, if the cell is past the G1 checkpoint it completes the cell cycle and enters $G_0$ upon reaching G1). When quiescent $G_0$ cells are compared with cycling cells, it is found that they are severely depleted in one or more types of Cdk protein and in all of the G1 cyclins (MBOC p. 897). When growth factors are once again available to $G_0$ cells, they require 8 hours to emerge from the $G_0$ state as they must spend time slowly reassembling the control system in order to begin cycling again.

3) Direct and Indirect Action Against Angiogenesis

Cancer also involves another process that is dependent on hyperactive protein synthesis and hyperactive cell proliferation: angiogenesis. Angiogenesis is the growth of new blood vessels.

The naturally occurring balance between stimulators and inhibitors of angiogenesis in the human body is one in which inhibitory influences predominate. The rare instances in which angiogenesis occurs under normal conditions are wound healing, organ regeneration, embryonic development, and female reproductive processes. Also, when cells are deprived of oxygen, they release angiogenic factors that induce new capillary growth which is why nearly all vertebrate cell are located within 50 $\mu$m of a capillary. A typical cell is ~15 $\mu$m, which would mean that by the time a cell is surrounded by ~4 or so new cells on all sides (~100 $\mu m^2$ mass) it would be deprived of oxygen and begin issuing signals (protein growth factors) for initiation of angiogenesis.

Unnatural or disease conditions that involve angiogenesis include cancer. As tumor cells crowd each other, crowded tumor cells become deprived oxygen and send out signals (i.e. begin accelerated production of protein growth factors for angiogenesis) to the nearby endothelial cells (cells that form the wall of blood vessels). A normally dormant endothelial cell becomes activated, secretes enzymes that degrade the extracellular matrix (the surrounding tissue), invades the matrix, begins dividing and eventually the new endothelial cells organize into hollow tubes creating new networks of blood vessels. Normally endothelial cells are quiescent: however they can show a 100 fold increase in proliferation during neovascularization (HPIM p. 521). It is known that tumors become vascularized at a size of less than 1250 $\mu m^2$ (HPIM p. 521). Without angiogenesis a tumor cannot grow beyond the size of a pinhead (~1 to 2 cubic millimeters) (NCI website). Tumor growth is logarithmic and the induced angiogenesis is proportional to tumor growth.

About 15 growth factor proteins are known to activate endothelial cell growth and movement, including angiogenin, epidermal growth factor, fibroblast growth factors, interleukin 8, prostaglandin E1 and E2, tumor necrosis factor-a, vascular endothelial growth factor (VEGF), and granulocyte colony stimulating factor.

Trichothecene administration would thus function two ways to inhibit angiogenesis. First, it would be directly cytotoxic to rapidly proliferating endothelial cells by the same direct mechanisms described above for cancer cells. Second, it would inhibit the excessive production of protein growth factors by oxygen starved tumor cells that initiate angiogenesis. Inhibiting angiogenesis would not only starve the tumor of oxygen and nutrients but also reduce the probability of metastasis as cancer cells use the circulatory system as a pathway to travel to distant sites.

4) Action Against Multi Drug Resistance

Because of the abnormally high mutability of many cancers, most malignant tumor cell populations are heterogeneous in many respects and capable of evolving at an alarming rate when subjected to new selection pressures. Repeated treatments with drugs that are selectively cytotoxic to dividing cells can be used to kill the majority of neoplastic cells in a cancer patient, but it is rarely possible to kill them all. Usually some small proportion are drug-resistant, and the effect of the treatment is to favor the spread and evolution of cells with this trait (MBOC p. 1271).

The phenomenon of multidrug resistance is frequently correlated with a curious change in the karyotype: the cell is seen to contain additional pairs of miniature chromosomes or to have a homogeneously staining region interpolated in the normal banding pattern of one of its regular chromosomes. Both these aberrations consist of massively amplified numbers of copies of a small segment of the genome which often contains a specific gene, known as the multidrug resistance (mdr1) gene which codes for a plasma-membrane-bound transport protein ATPase (MBOC pgs. 1271–1272). ATPases are a diverse family of transport proteins and overexpression of MDR protein in human cancer cells enables them to pump drugs out of the cells (MBOC p. 520).

As protein synthesis inhibitors, composition of present invention would inhibit overexpression of MDR proteins, disabling the ability of cancer cells to pump out the chemotherapeutic(s). Prior art chemotherapeutics do not have this ability because of their single, narrow mechanisms of action as described earlier in this application. Furthermore, prior art chemotherapeutics act to selectively favor the propagation of MDR cells when they are present.

5) Prophylactic Action Against Chemotherapeutic Injury Response

Current thinking hypothesizes that after chemotherapy, in the interim periods of cyclical administration, there is a natural body response to "chemotherapeutic injury". Lymphocytes responding to the "chemotherapeutic injury" produce interleukins, which are known to include growth factors including angiogenesis stimulating growth factors (see Magainin Pharmaceuticals injured tumor "Synergy Hypothesis" and supporting data enclosed).

Because of novel administration methods provided in present invention and the absence of appreciable systemic cytotoxicity, compositions of present invention would be administered fairly continuously (~2 to 7 day "off" periods) versus the fairly long periods (~21 or 28 day "off" periods) of prior art chemotherapeutics (that long time period allowing the body's "injured tumor" response to be of consequence). Because of fairly continuous administration of compositions of present invention, any potential "injured tumor" regrowth response would be inhibited or muted.

6) Special Situations—Large Tumors

Although the above mechanisms of action apply generally to all cancers, there are special situations where compositions and methods of present invention provide novel therapeutic advantages, heretofore not available in prior art. One example is large tumors.

Patients with large tumors often respond poorly to chemotherapy, primarily because of unfavorable tumor cytokinetics (HPIM p. 527). Large tumors are accompanied by large internal pressures that prevent blood, and consequently blood carried chemotherapeutics, from reaching cancer cells effectively. Compositions of present invention are injected directly into the tumor and travel through the gap junctions so they are not impacted by the poor circulation issue. Furthermore, the lack of blood flow in the tumor actually aids in preventing therapeutics of present invention form reaching general circulation. Killing off a given percentage of the tumor with compositions of present invention would relieve internal pressure and enhance subsequent delivery and efficacy of chemotherapeutics administered via the circulatory system.

In summary, the administration of therapeutically effective amounts of trichothecenes by interstitial injection to a person afflicted with cancer would have the following beneficial effect: 1) direct cytotoxicity to cancer cells by multiple mechanisms of action, 2) inhibition of excessive production of protein growth factors produced by cancer cells for continued tumor growth (i.e. inhibition of oncogene products), 3) inhibition of excessive endothelial protein growth factor production by cancer cells for stimulating angiogenesis to support tumor growth, 4) direct cytotoxicity to rapidly proliferating endothelial cells required to support tumor growth, 5) dismantling the cell cycle control system, 6) inhibition of MDR protein production in tumors possessing such cells, and 7) inhibition of potential immune system induced "injured tumor" response. Additionally, in large tumors therapeutics of present invention could be used to reduce tumor size and internal pressure so enhance delivery of conventional chemotherapeutics via the circulatory system.

SUMMARY OF THE INVENTION

The present invention provides compositions and methods for treating cancer by substantially interstitial administration of therapeutic(s) of invention directly into the tumor and surrounding tissue.

Objects of Invention

It is an object of the invention to provide a therapeutic that can be administered by injection, or other localized substantially interstitial perfusion method, to inhibit proliferation of cancer cell populations in the area under treatment without inducing appreciable systemic cytotoxicity.

It is an object of the invention to provide a therapeutic that can be administered by injection, or other localized substantially interstitial perfusion method, to kill or inhibit proliferation of cancer cells, to kill or inhibit cancer induced endothelial cells in proximity to the cancer cells, to inhibit production of growth factors by cancer cells including both oncogene produced growth factors and angiogenic growth factors, to dismantle the cell cycle control system, to inhibit production of MDR proteins by certain cancer cells, to inhibit regrowth effects initiated by leucocyte cells as part of a "injured tumor" response, and to accomplish all this without inducing appreciable systemic cytotoxicity or appreciable toxicity to normal tissue in the area of the tumor.

It is an object of the invention to inhibit tumor growth and related angiogenesis.

It is an object of current invention to provide means of prolonging a patient's life, wherein said patient has inoperable tumor(s) or tumors that are resistant to existing chemotherapy.

DETAILED DESCRIPTION OF INVENTION

The treatments disclosed below involve administration of biologically active trichothecenes by injection directly into a tissue mass, or other method of interstitial perfusion, to inhibit the growth of cancer cell populations in the area under treatment, while preventing appreciable systemic cytotoxicity, and while also preventing or minimizing toxicity to local tissue. Materials and methods for achieving this are described below.

Reduction to Practice—Compositions for Use in Therapeutics of Present Invention

Because of the novel administration method, rapid internalization and localization are important attributes for selecting the appropriate trichothecenes that heretofore had not been a consideration. Preferred embodiment favors macrocyclic trichothecenes (vs. simple trichothecenes as tested in prior art) because of the enhanced cellular internalization afforded by the macrocyclic ring, however nothing in this application is intended to limit the scope of trichothecenes that may be used. The ability to use localized, tissue side administration is based, in part, on trichothecene's ability to rapidly internalize through cell membranes and, in part, on trichothecene's ability to "localize" within a tissue mass or organ.

Okazaki et.al. and Tani et.al. showed, in vitro, the ability of trichothecenes to be rapidly "internalized" through human cell membranes. Trichothecenes are also one of the few toxins that are dermally active possessing the ability to penetrate and internalize in the skin (e.g T-2, in AMRIID's "Understanding the Threat"). Certain trichothecenes are even capable of being inhaled in their raw form and penetrating the aerodigestive epithelium (e.g. Satratoxin H, from University of Minnesota, Department of Environmental Health and Safety web page).

Trichothecene's "localization" attribute has been demonstrated in animal models by AMRIID. Although trichothecene mycotoxins have been described in U.S. Pat. Nos. 4,906,452 and 4,744,981 as "the most toxic molecules that contain only carbon, hydrogen, and oxygen, some being 10-fold or greater more potent than actinomycin, the most potent per weight of the chemotherapeutic drugs currently approved for clinical use" when AMRIID (in AMRIID's "Understanding the Threat") administered them to mice in aerosol form (i.e. effectively tissue side administration), trichothecene came in as the absolute poorest toxin on the list of 25 tested (AMRIID's "Understanding the Threat", table 2, third page) and AMRIID concluded "Aerosol toxicities are generally too low to make this class of toxins useful to an aggressor" (AMRIID's "Understanding the Threat", page 4). This corroborates the ability of trichothecene to be rapidly absorbed and retained by the tissue it comes into contact with (i.e. lungs in this case, which fortunately is not a rapidly proliferating tissue in adults) and prevented from reaching systemic circulation where its cytotoxic effects are well known and severe to rapidly proliferative cells such as bone marrow and gastrointestinal mucosa.

An even more compelling, in vivo, corroboration of the localization attribute comes from a cluster of 10 infant deaths in a suburb of Cleveland in 1995 (NIEHS press release). The infant deaths turned out to be caused by inhalation of airborne fungal mycotoxins produced by the fungus Stachybotrys atra. Stachybotrys atra (a.k.a. stachybotrys chartarum) which produces trichothecene mycotoxins including satratoxins G, H, and F, roridin E, verrucarin J, and trichoverrols A and B. The cluster of infant deaths in Cleveland demonstrated, in vivo, in humans, the ability of trichothecenes to internalize and localize in lung tissue (albeit destroying the rapidly proliferating lung tissue in infants but not destroying adult lungs that are no longer rapidly proliferating) and without appreciably entering general circulation as evidenced by the absence of noticeable systemic cytotoxicity in either infants or adults.

The likely molecular basis for "localization" is trichothecene's macrocyclic ring that enhances cell binding and internalization (by an MOA not yet fully understood), combined with the molecule's relative insolubility in water which would tend to keep it out of general circulation, and combined with the molecules small size which would facilitate gap junction intra organ, or intra tissue mass, transport. Once internalized, trichothecene would be limited to transport within the organ or tissue mass through the gap junction transport system. Cells of an organ are joined together by gap junctions which allow for sharing of small molecules such as sugars, amino acids, and nucleotides (MBOC pgs. 958–959). The gap junctions allow molecules smaller then ~1000 daltons to pass and trichothecenes are comfortably under the size limitation at 250–700 daltons.

Representative examples of compositions suited for use in an embodiment of current invention can be gleaned from the above examples and include satratoxins G, H, and F, roridin E, verrucarin J, and trichoverrols A and B because of their demonstrated rapid internalization and localization attributes. Alternatively, methods for selecting suitable compositions for localized administration under current invention are disclosed below.

Reduction to Practice—Alternative Method for Selecting Composition for Use by Present Invention An "internalization profile" would be created for each likely member of the trichothecene family considered for administration. This would be created by in vitro testing of each trichothecene against a panel of both normal and malignant human cell lines.

Trichothecene mycotoxins can be purchased from companies such as Sigma Chemical Co. St. Louis Mo., USA or Wako Pure Chemical Industries, Ltd., Japan, or Wellcome Research Laboratories, Buckinghamshire, England or Boehringer-Mannheim, Manheim, West Germany. Alternatively, the appropriate fungi can be grown in culture and the trichothecenes extracted by centrifugal partition chromatography as described in Tani et. al. and described in other literature such as Onji et. al. (Onji, Y., Aoki, Y., Yamazoe, Y., Dohi, Y., and Moriyamam, T., 1988 *Isolation of nivalenol and fusarenon-X from pressed barley culture by centrifugal partition chromatography, Journal Liquid Chromatography*, 11:2537–2546) or Jarvis et al. (Jarvis, B. B., R. M. Eppley, and E. P. Mazzola, 1983 *Chemistry and Bioprodiction of the Macrocyclic Trichothecenes*, p 20–38. In Y. Ueno, Trichothecenes: chemical, biological, and toxicological aspects, vol 4. Elsevier Science Publishing Inc., New York) or Sorensen et al. (Sorenson, W. G., Frazer, D. G., Jarvis, B. B., Simpson, J., and Robinson, V. A., *Trichothecene Mycotoxins in Aerosolized Conidia of Stachybotrys atra*, June 1987 *Applied and Environmental Microbiology*, Vol. 53 No. 6, p. 1370–1375) where S. atra was grown on sterile rice, autoclaved, dried, and then aerosolized by acoustic vibration and collected on glass-fiber filters.

Human cell lines are commercially available from several sources including ATCC—American Type Culture Collection, Manassas, Va., USA or ECACC—European Collection of Cell Cultures, Salisbury, Wiltshire, UK or DSMZ—German Collection of Microorgainisms & Cell Cultures, Braunschweig, Germany or IZSBS—Istituto Zooprofilattico Sperimentale, Brescia, Italy or ICLC—Interlab Cell Line Collection, Genova, Italy or ECBR—European Collection for Biomedical Research, Genova, Italy or any other suitable supplier. Human cell lines available include both normal and malignant cell lines.

Each trichothecene selected for consideration would then be administered to a panel of culture dishes containing various normal and malignant cell lines to establish internalization proclivities for each trichothecene to various cell types. The cell lines could be grown in culture and exposed to various trichothecenes by methods described in Okazaki et al. or Tani et al. where human cell lines were grown in Eagle's minimum essential medium (MEM) supplemented with 10% fetal calf serum (FCS). Trichothecenes were dissolved in dimethyl sulfoxide at a concentration of 20 mg/ml and diluted in Eagle's MEM. Stock solutions (200 µg/ml) were prepared, passed through a 450-nm Millipore membrane filter and stored at −20° C. until use. Tissue culture plates would be seeded with a panel of normal and malignant human cell lines which would be allowed to proliferate at 37° C. until confluent monolayers had formed. They would then be exposed to concentrations of the trichothecene known to have efficacy against hyper protein synthesizing cells and non cytotoxicity to non hyper protein synthesizing cells (e.g. ~10 ng/ml for satratoxin and roridin macrocyclic trichothecene sub families, ~100 ng/ml for baccharinoids, ~200 ng/ml for Group A simple trichothecenes, etc.) however any other suitable concentration may be chosen. After 1 hour, or other suitable time increment or increments, the trichothecene solution would be tested to determine the concentration that remained in solution to determine how much had been absorbed by the human cell line.

An "absorbency" or "cellular internalization table" would be constructed from this data. Such a table would show the percentage of trichothecene in the original solution that was internalized by a given cell line within the given time increment or increments. Trichothecenes demonstrating the greatest internalization rates for a given cancer cell line would move on to therapeutic index dosage profiling (described in detail later) for that cancer type. Trichothecenes demonstrating high cellular internalization rates for a given cancer and low cellular internalization rates for a given normal cell type, wherein said cancer cell was likely to metastasize to a distant site containing said normal cells, would be special class of "double index" injectable therapeutics in applications involving the above circumstances in vivo. Normal chemotherapeutics rely only on a therapeutic index based on cell cycle activity differentials between cancer and normal cells. The "double index" situation of current invention described above would be much more powerful in that it would not only have the benefit of the cell cycle activity differential but the advantage of the cellular internalization differential, when used with a cancer cell type that readily internalizes the trichothecene that has metastasized to a site comprised of tissue that internalizes the trichothecene less readily. The "double index" part is only achievable with localized administration since in systemic administration, the therapeutic would have to have as large of an internalization differential with every possible cell type it could encounter, including the cell type from which the cancer originated in the first place.

Reduction to Practice—Dosage Determination of Selected Compositions

Compositions selected for use, under any method, or no method, would then be subject to testing for determination of therapeutic index and "maximum tolerated dose" as defined in prior art. Methods for constructing a useful therapeutic index for various trichothecenes, against cell populations exhibiting a hyperactive state of protein synthesis, and without toxicity to non hyperactive cells, have been established, in vitro, in analogous models of virally infected cells. Detailed methods of in vitro procedures for determining trichothecene dosage dependent inhibition of target cell populations are provided in Okazaki et al. (Okazaki, K., Yoshizawa, T., and Kimura, S. 1989 *Antiviral Activity of Macrocyclic Trichothecene Mycotoxins and Related Compounds Baccharinoids B-4 and B-5 Against Herpes Simplex Virus Type 2, Agricultural and Biological Chemistry* 53 pages 1441–1443) or Okazaki et al. (Okazaki, K., Yoshizawa, T., and Kimura, S. 1988 *Inhibition by Trichothecene Mycotoxins of Replication of Herpes Simplex Virus Type 2, Agricultural and Biological Chemistry* 52 pages 795–801) or Tani et al. (Tani, N., Dohi, Y., Onji, Y., and Yonemasu, K., 1995 *Antiviral activity of Trichothecene Mycotoxins against Herpes Simplex Virus Type 1 and 2, Microbiol. Immunol.*, 39(8), pages 635–637) enclosed, and incorporated herein by reference.

Various human cancer and normal human cell lines would be substituted in place of the virally infected cells used in either Okazaki or Tani. The same methods for applying various concentrations of trichothecenes and measuring cell mortality by trypan blue exclusion after trypsinization by could be used, however any suitable method may be substituted to determine the percentage of cell mortality at various concentration of trichothecene. This data would then be used for constructing the "Tumor Response Profile" and "Normal Response Profile" as shown in Harrison's Principles of Internal Medicine page 528, FIG. 86-3. These two profiles would then be used in computation of the "Therapeutic Index" and "maximum tolerated dose" as established in prior art practice of dosage determination and described in Harrison's Principles of Internal Medicine's principles of pharmocodynamics, pages 527–528, incorporated herein by reference.

It should be noted that computation of the "maximum tolerated dose" under present invention would be location specific. As an example, treatment for a specific type of lung cancer cell would use the same "Tumor Response" profile, however the "Normal Tissue Response" profile used would depend on the normal tissue in the location in which the lung cancer cell had metastasized (e.g. liver, brain, etc . . . ). Thus the "maximum tolerated dose" could be different for the same type of lung cancer cell in two different metastatic sites.

Currently, new anti tumor compounds are first tested against about 60 human cancer cell lines. Agents demonstrating in vitro antitumor activity are then tested against a panel of human tumor xenografts in nude mice (HPIM p. 534). Dosage determination and safety is further refined in Phase I human clinical trials and efficacy is further refined in Phase II. Present invention envisions following conventional, prior art, NCI protocols in these areas.

Reduction to Practice—Redefining Cyclical Administration

Because of the novelty of compositions and administration methods of present invention, cyclical administration methods need to be redefined in part. Although in vitro testing can yield 100% cytotoxicity to a cancer cell populations, in vivo administration typically results in something less and as such multiple administrations are required as previously described to get below the theoretical one surviving cell number.

Under prior art, chemotherapeutics are administered in cycles as previously described. Most regimens are administered in cycles of 21 to 28 days to allow blood counts to recover from chemotherapy—induced bone marrow suppression. The period when chemotherapeutic administration is suspended to allow blood cell counts to recover is hereinafter referred to as the "interim" or "off" period.

Since compositions and administration methods of present invention do not induce appreciable systemic cytotoxicity, the limiting factor for duration of administration would be based on cytotoxicity to the surrounding tissue and need for recovery time of said tissue. In most cases however, such tissue will not be actively cycling and the limiting factor will instead be related to a brief respite between administration cycles to insure any surviving cancer cells have had time to intracellularly inactivate the trichothecene (by conversion to apotrichothecenes as previously mentioned), reassemble their cell cycle control systems (~8 hours), and start cycling again.

The time period between administrations could thus be determined in vitro. For a given cancer cell line or type, a slightly lower dose than the maximum tolerated dose would be administered to cells in culture by methods previously described. The cells would then be observed over time to determine the amount of time it took until any surviving cells started cycling again. This "biologically active period" of trichothecene would determine the frequency of administration of the trichothecene. Successive administrations could not be spaced closer than the "biologically active period". As an example, if the selected trichothecene killed 95% of a cancer cell population in vitro within 24 hours of administration, and the surviving 5% cells did not resume cycling again for another 24 hours, the minimum time between administrations would be 2 days and a prudent time between administrations would be several days (e.g 3 to 7 days). However, any other suitable methods or procedures may be substituted to determine timing between successive administrations of trichothecene.

PET scans using positron emitting glucose, or any other suitable method or imaging technology, may be used to corroborate efficacy of an administration as well as the timing of when any surviving cancer cells start cycling again, in vivo.

The number of such cycles to be used would be computed using the Skipper "log cell kill model" described in the "Principles of Chemotherapeutic Administration" section of this application. Utility under this method could also be corroborated in vivo by PET scans and positron emitting glucose, however any other suitable method or imaging technology may be substituted.

Reduction to Practice—Administration Method

Preferred embodiment combines trichothecene with propylene glycol ($CH_3CHOHCH_2OH$), or any other suitable solvent, to form a "pharmaceutical composition" suitable for administration by hypodermic needle, or any other suitable device capable of localized, predominantly interstitial drug delivery. Propylene glycol is commonly used as a solvent for parenteral administration and is generally considered as safe by the FDA. Trichothecene is also soluble in ethanol and dimethyl sulfoxide, which may be used in place of propylene glycol where suitable, as well as in conjunction with other inert liquids or gels. As used in present invention, solvents serve no biological purpose other than to facilitate substantially homogeneous spatial distribution of trichothecene(s).

Nothing in this application or its related claims is intended to limit the solvent used to propylene glycol. Nothing in this application or its related claims is intended to limit pharmaceutical compositions to just propylene glycol (or other solvent or carrier) and trichothecene. The present invention also envisions mixing the trichothecene with other compounds or substances, including combinations of trichothecenes, to facilitate administration, facilitate or regulate the rate and/or depth of penetration and/or absorption of said trichothecene mycotoxins, increase efficacy of said mycotoxins, provide prophylactic activity against infection, or provide any other beneficial or synergistic function. The compounds collectively described above are herein also termed "pharmaceutical compositions". As an example, a combination of macrocyclic and simple trichothecenes may be used to achieve more extensive penetration (as macrocyclics internalize faster and simple trichothecenes would migrate further before internalization). As another example, antibiotics may be included as part of the pharmaceutical composition. As another example pharmaceutical compositions may include other protein synthesis inhibitors or angiogenesis inhibitors such as squalamine or troponin. As another example pharmaceutical compositions may include chemotherapeutics that work by different mechanisms of action than trichothecene. Pharmaceutical compositions may also include any other substances that facilitate absorption or increase efficacy or safety of therapeutics of present invention, provide other prophylactic activity, or provide any other beneficial or synergistic function or substances that facilitate imaging equipment to image the tumor or tumor response to compositions of present invention.

The preferred embodiment of present invention uses Positron Emission Tomography (PET) with a glucose tracer to identify the locus of tumors however any other suitable imaging technology may be used to identify the locus of tumors or facilitate in administration of compositions of present invention into the locus of tumors. In the preferred embodiment pharmaceutical compositions of present invention are administered directly into a tissue mass by one or more hypodermic injections, wherein each injection is preformed continuously as the hypodermic is being retracted, to achieve a substantially columnar dispersion of compositions into the tissue mass and without significant concentrations potentially being administered into outbound vascularization. Alternatively, hand held devices capable of delivering the contents of a hypodermic needle over a three dimensional substantially columnar area in a tissue mass have also been designed by applicant and are anticipated to be filed under a separate patent application in the future as well as mechanical devices capable of uniform, localized drug delivery into a user definable, three dimensional area within a tissue mass have already been filed. However, any other suitable device or means may be used to physically administer pharmaceutical compositions of present invention.

EXAMPLE 1

Use in Breast Cancer Instead of Surgery and Systemic Chemotherapy

As and example, a Stage III locally advanced breast cancer is diagnosed with ancillary lymph node involvement. Prior art treatment (HPIM pgs. 566–567) recommends multi modality clinics to coordinate systemic chemotherapy (multidrug, including an anthracycline), surgery, and radiation therapy, combined to produce long term disease-free survival in about 30 to 50 percent of patients.

Under present invention, the maximum tolerated dose (as previously described) of Roridin A (however any other suitable trichothecene(s) or suitable lower dose may be substituted) combined with propylene glycol (however any other suitable solvent or carrier may be used) are placed in hypodermic needles and administered to the tumor, lymph nodes, and surrounding breast tissue using a plurality of hypodermic injections, each said injection maximizing area of dissemination by injecting therapeutic continually as the hypodermic is being retracted. Such continual administration of therapeutic as the hypodermic is being retracted may be approximated manually or aided by the use of hand held or mechanically operated devices designed to provide a substantially columnar 3 dimensional interstitial dispersion of therapeutic with each injection, however any other suitable administration means may be used. The process is repeated for 8 cycles (or other suitable number as determined by methods previously described), each cycle spaced 7 days apart (or other suitable time periods, but not less than the "biologically active period" as previously described). Several weeks after all administration cycles have been completed, a PET scan (or any other suitable imaging technology) is used to confirm the absence of any remaining malignant cells.

In stark contrast to prior art, the full 8 cycle administration regimen of therapeutics of present invention can be administered in 2 months (or less) versus ~8 months for prior art chemotherapeutics. Compositions and methods of present invention will not induce appreciable systemic cytotoxicity to normal rapidly proliferating tissue versus prior art compositions and methods. Surgery and radiation therapy may be obviated completely.

EXAMPLE 2

Synergistic Use With Prior Art Chemotherapeutics

A PET scan reveals a chain of lymph node tumors in the neck and chest (e.g. page 2 of UCLA PET brochure enclosed). Therapeutics of present invention are injected into the tumor masses and surrounding tissue (by hypodermics as described above) for one cycle. Conventional systemic chemotherapy is then administered under prior art methods and practices.

In this example the purpose of administering therapeutics of present invention is to reduce the initial tumor mass and internal pressure which in turn would enhance delivery of conventional systemic chemotherapeutics by the circulatory system. Additionally, the "injured tumor" response would invoke accelerated growth effects in cells that would now make those cells (e.g. endothelial) more susceptible to cell-cycle active chemotherapeutics. Lastly, if there is a MDR cell or cells in the population, it would either be killed by therapeutics of present invention or have the MDR protein product suppressed temporarily if it survives (allowing better intracellular accumulations of the subsequently administered conventional chemotherapeutic).

OTHER APPLICATIONS AND EMBODIMENTS

Although the preferred embodiment of present invention focuses on use of therapeutics for treatment of cancer, nothing is intended to preclude the use of current invention for other conditions or disorders that could benefit from localized hyperactive protein synthesis inhibition.

One such example is fibrodysplasia ossificans progessiva (FOP) where bone replaces tendons, fasciae, and ligaments. FOP is easily triggered by injury and minor bumps can result in large bone structures forming at the injury site. In FOP patients, lymphocytes responding to such an injury move out to the muscle cells, start killing them, and produce bone morphogenic protein (BMP). As BMP levels rise bone growth ensues. Angiogenesis has also been observed to be a requisite part of the process for this transformation. Currently no methods exist for preventing the transformation. Interstitial administration of compositions of present invention directly into the injury site would inhibit BMP protein production as well as angiogenesis.

Novelty and Unobviousness

In summary, the current invention is unobvious and novel over prior art for several reasons. First, it reverses the direction of administration over prior art, going from tissue to blood versus from blood to tissue in delivering therapeutic to target cell populations. Second, it uses the intercellular gap junction transport system for localized drug distribution versus the circulatory system as in prior art. Third, it embraces the use of non specific cellular internalization (exactly opposite from prior art) and aqueous insolubility to rapidly localize therapeutics of present invention into a tissue mass and prevent systemic distribution and related systemic cytotoxicity. Fourth, it provides novel, multiple mechanisms of action over other chemotherapeutics currently in use including: a) direct cytotoxicity to cancer cells by inhibiting multiple protein pathways required during the cell cycle, b) inhibiting oncogene growth factor products required for continued tumor growth, c) inhibiting angiogenesis by cytotoxicity to actively cycling endothelial cells, d) inhibiting production of angiogenic growth factors by cancer cells, e) dismantling the cell cycle control system through inhibition of cyclin production, f) preventing any potential "injured tumor" response that may enhance tumor regrowth and g) inhibiting MDR protein production in drug resistant cancer cells. Fifth, it provides a greatly reduced treatment regimen duration period over prior art chemotherapeutics (i.e. several weeks versus several months). Sixth, it will also provide novel synergistic uses in combination chemotherapy regimens including but not limited to a) destruction of portions of large tumors for enhanced delivery of conventional chemotherapeutics, b) destruction of MDR tumor(s) left by conventional chemotherapy, c) enhancing retention of conventional chemotherapeutics in tumors containing MDR cells. Lastly, compositions and methods of present invention provide a chemotherapeutic regimen that does not induce appreciable systemic cytotoxicity.

References Cited:

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th edition, McGraw Hill, 1998, Fauci, Braunwald, Isselbacher, Wilson, Martin, Kasper, Hauser, Longo.

I claim:

1. A method of inhibiting the proliferation of malignant cells in humans or non-human animals, comprising injecting of compositions containing therapeutically effective amounts of trichothecene(s), directly into a tumor in said humans or animals.

2. The method of claim 1 wherein said administration is by hypodermic injection or other means of delivering a drug interstitially into a tissue mass.

3. The method of claim 1 wherein said trichothecene is a macrocyclic trichothecene.

4. The method of claim 1 wherein said trichothecene is satratoxin G, H, or F, roridin E, verrucarin J, or trichoverrol A or B.

5. The method of claim 1 wherein said trichothecene is a fragment or sub-unit of trichothecene which still possesses the biological activity of inhibiting protein synthesis.

6. The method of claim 1 wherein said trichothecene is a molecule that contains a sesquiterpene epoxide structure and is capable of inhibiting protein synthesis.

7. The method of any one of claims 1 through 6 wherein said compositions include propylene glycol, ethanol, dimethyl sulfoxide or other solvent, carrier, or inert liquid or gel.

* * * * *